United States Patent [19]

Oki et al.

[11] 4,424,342

[45] Jan. 3, 1984

[54] ANTHRACYCLINE ANTIBIOTIC COMPOUNDS

[75] Inventors: Toshikazu Oki, Yokohama; Akihiro Yoshimoto, Fujisawa; Yasue Matsuzawa, Fujisawa; Tomoyuki Ishikura, Chigasaki; Hamao Umezawa; Tomio Takeuchi, both of Tokyo, all of Japan

[73] Assignee: Sanraku-Ocean Co., Ltd., Tokyo, Japan

[21] Appl. No.: 361,175

[22] Filed: Mar. 24, 1982

[30] Foreign Application Priority Data

Apr. 3, 1981 [JP]  Japan .................................. 56-49400

[51] Int. Cl.$^3$ ..................... C07H 15/24; A61K 31/71; C12P 19/56
[52] U.S. Cl. ..................... 536/6.4; 424/180; 435/78
[58] Field of Search .................. 536/6.4; 424/180

[56]  References Cited

U.S. PATENT DOCUMENTS 4,267,312  5/1981  Oki et al. ............................ 536/6.4
4,316,011  2/1982  Oki et al. ............................ 536/6.4

Primary Examiner—Johnnie R. Brown
Assistant Examiner—Elli Peselev
Attorney, Agent, or Firm—Jordan and Hamburg

[57]  ABSTRACT

Disclosed are an antitumor compound having the chemical structure

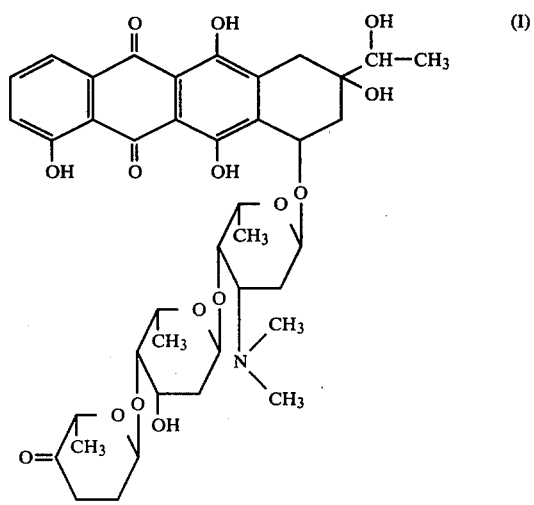

or its acid addition salts; and its preparation method which consists of treating a compound represented by the chemical structure

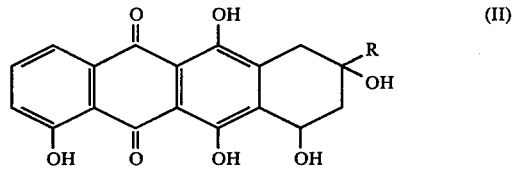

wherein
R is a COCH$_3$ or CH(OH)CH$_3$ group,
by a streptomycetes strain or its mutants.

1 Claim, No Drawings

ANTHRACYCLINE ANTIBIOTIC COMPOUNDS

BACKGROUND OF THE INVENTION

1. Field of the Invention

The present invention deals with a novel anthracycline antibiotic with potent antitumor activity having the chemical structure

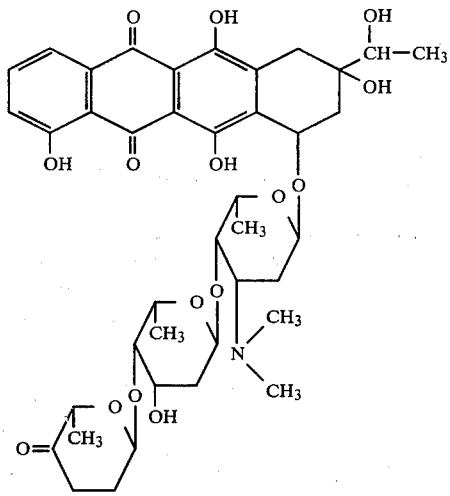

and a biochemical method for production of said compound.

2. Description of the prior art

It is well known that antibiotics containing as aglycone the anthracyclinone structure represented by the following formula

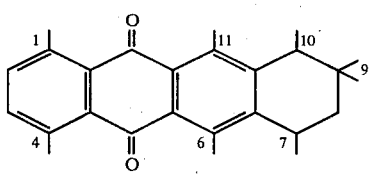

generally have a potent antitumor activity against various experimental neoplasms in animals. Thus various anthracycline compounds have been provided by fermentative, semi-synthetic and fully synthetic methods (for example, adriamycin in U.S. Pat. No. 3,590,028; carminomycin in J. Antibiotics 27, 254 (1974); dihydrocarminomycin in Antibiotiki 21, 1008 (1976); rhodomycin antibiotics in E.P.O. Laid-Open Publication No. 0022574 dated Jan. 21, 1981; review on anthracycline antibiotics in The Japanese Journal of Antibiotics 30, S-70 (1977)).

SUMMARY OF THE INVENTION

The present invention provides a novel antitumor antibiotic having the chemical structure

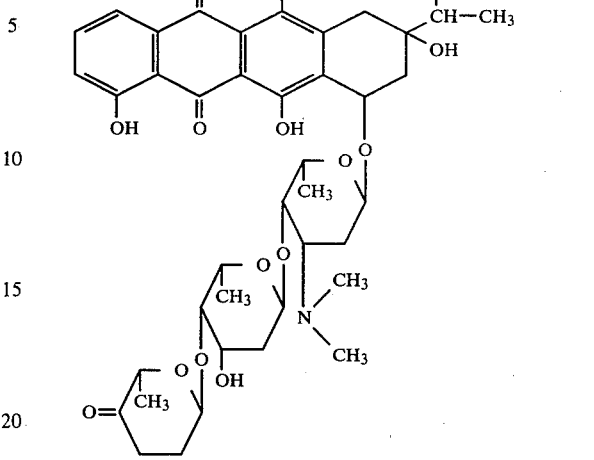

which finds practical utility in the chemotherapy of tumors.

The present invention also provides a method for preparation of the antibiotic represented by structure (I) or its acid addition salts which consists of cultivating a streptomycetes strain capable of converting a compound represented by the chemical structure

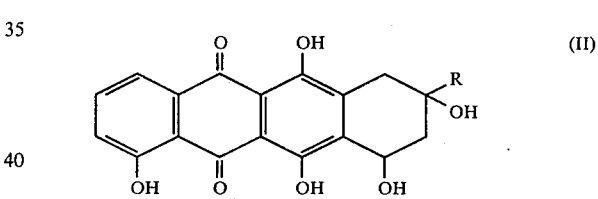

wherein

R is a $COCH_3$ or $CH(OH)CH_3$ group, to the antibiotic represented by structure (I), in a medium composed of carbon sources, nitrogen sources, mineral components and trace elements; adding the compound represented by structure (II) at a suitable stage of growth; and continuing the incubation of the mixture until a substantial amount of the compound represented by structure (I) is accumulated in the broth whereby said antibiotic is isolated and/or transformed into acid addition salts by conventional methods.

DETAILED DESCRIPTION OF THE INVENTION

The present invention relates to a novel anthracycline antibiotic having potent antitumor activity. More particularly, it relates to an antibiotic represented by the chemical structure

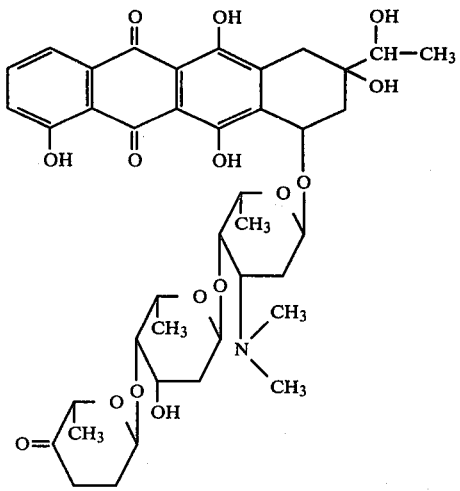

or its acid addition salts;
and its preparation method.

The antibiotic represented by structure (I) of the present invention is a novel anthracycline compound which is hitherto unknown in the literature. Its structural characteristic resides in the glycoside moiety having the following formula

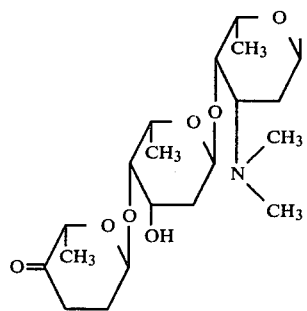

in which L-rhodosamine (in dihydrocarminomycin, this is replaced by daunosamine shown below

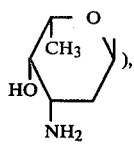

2-deoxy-L-fucose and L-cinerulose A are bound through the glycoside bondage. This antibiotic will be referred to as "trisarubicinol" hereafter.

The novel anthracycline antibiotic represented by structure (I) has a strong therapeutic effect on mouse leukemia (L1210) and shows excellent antitumor activity on various experimental tumors in animals. Because of its unique low toxicity, this antibiotic is advantageously employable as antitumor agent.

The 3'-dimethylamino group of trisarubicinol may be in form of acid addition salts. Among such salts, those with pharmaceutically permissible acids are favorable. For example, hydrochloride, sulfate, hydrobromide, nitrate, phosphate, acetate, propionate, maleate, oleate, citrate, tartarate, fumarate, glutamate, pantothenate, laurylsulfonate, methanesulfonate and naphthalenesulfonate are advantageously employed.

Microorganisms employable in the present invention can be selected from a wide range of microorganisms as far as they have an ability to convert an anthraclinone compound represented by the chemical structure

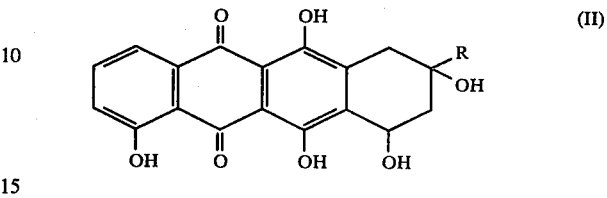

wherein
R is a COCH$_3$ or CH(OH)CH$_3$ group (compound (II) is carminomycinone when R is COCH$_3$; and dihydrocarminomycinone when R is CH(OH)CH$_3$), to trisarubicinol.

In the following, a method for screening suitable strains for the execution of the present invention will be explained. By such method, those skilled in the art can easily obtain strains employable in the present invention.

Microorganisms capable of producing aclacinomycin such as *Streptomyces galilaeus* MA 144-M1 (ATCC 31133; FERM-P 2455) are usable in the present invention. In addition, employable are various mutants that can be derived from such microorganisms by physical treatment with ultraviolet, alpha, gamma and X rays and by chemical treatment with mutagens such as nitrosoguanidine and diepoxybutane. For example, mutant strain KE 303 (FERM-P 4808) derived from *Streptomyces galilaeus* MA 144-M1 (ATCC 31133; FERM-P 2455) is one of the most preferably usable organisms in the present invention. This mutant was obtained by the following method: spores of *Streptomyces galilaeus* collected from the YS agar slant culture were lightly dispersed by ultrasonication and then treated with 1000 µg/ml of N-methyl-N'-nitro-N-nitrosoguanidine. After collection by centrifugation, the treated spores were spread on YS agar medium. Each colony appearing on YS agar medium was inoculated both on an agar slant and in a flask containing seed medium. The seed flask was cultivated and further propagated in production medium. Mycelia were collected from broth and then subjected to extraction with an organic solvent. The organic extract was checked by spectrophotometry for production of yellow pigments ascribable to aclacinomycins. The yellow pigment-less (or anthracycline-nonproducing) colonies were picked and cultivated under shaking in production medium containing aklavinone. Among the pigment-less colonies, only those which had an ability to produce aclacinomycin A from aklavinone were selected for usage in the present invention.

*Streptomyces galilaeus* KE 303 (FERM-P 4808) possesses the following morphological, cultural and physiological properties which are very similar to those of the parent strain, except a small difference in the color of substrate mycelium. It is needless to say that other mutants can be derived for the present invention from aclacinomycin-producing organisms, as far as they have an ability to produce anthracycline glycosides from anthracyclinone (substrate) in spite of incapability to produce anthracycline glycosides by themselves.

1. Morphological properties

Microscopic observation shows open spirals developed well from branched substrate mycelium. No whorls are seen. Spores with smooth surface are ellipsoidal in shape and 0.4–0.8×0.8–1.6 μm in size, occurring in chains of more than ten. No sporangium and sclerotium are observed. This strain is assigned to the section Spirales of genus Streptomyces.

2. Cultural properties

The following readings were taken after two weeks of incubation at 27° C., unless specified otherwise. The color designations in parenthesis are in accordance with the definitions of the "Color Harmoney Manual" (Container Corporation of America, U.S.A.).

(1) Sucrose-nitrate agar
Vegetative growth—White to pale yellow (2db)
Aerial mycelium—None
Soluble pigment—None
(2) Glucose-asparagine agar
Vegetative growth—Pale yellow (1ba) to pale yellowish green (1½ec)
Aerial mycelium—Light gray (d)
Soluble pigment—None
(3) Glycerol-asparagine agar (ISP medium No. 5)
Vegetative growth—Pale yellowish green (1cb) to light grayish olive (1½ge)
Aerial mycelium—Yellowish gray to light gray (2dc)
Soluble pigment—None
(4) Starch-inorganic salts agar (ISP medium No. 4)
Vegatative growth—Pale yellow (1ba) to pale yellowish green (1cb)
Aerial mycelium—Medium gray (2fe; covert gray) to gray (d)
Soluble pigment—None
(5) Tyrosine agar (ISP medium No. 7)
Vegetative growth—Light grayish yellowish brown (3ge) to grayish brown (4li)
Aerial mycelium—Pale yellow at a later stage of growth
Soluble pigment—Black
(6) Nutrient agar
Vegetative growth—Grayish yellow (3ec)
Aerial mycelium—Yellowish gray (2dc) to light gray (d)
Soluble pigment—Brown
(7) Yeast extract-malt extract agar (ISP medium No. 2)
Vegetative growth—Pale olive (2gc) to pale Yellowish green (1½ec)
Aerial mycelium—Light brownish gray (3fe; silver gray) to dark gray (3ih; beige gray)
Soluble pigment—None or slightly brown
(8) Oatmeal agar (ISP medium No. 3)
Vegetative growth—Pale yellow (2db) to grayish yellow (3ec)
Aerial mycleium—Yellowish gray (2dc) to light gray (d)
Soluble pigment—Brown 3. Physiological properties (1) Growth temperature
When examining on maltose-yeast extract agar (1.0% maltose, 0.4% yeast extract (Oriental Yeast Co.), 3.5% agar; pH 6.0) at temperatures of 20°, 24°, 27°, 30°, 37° and and 50° C., the optimal growth temperature was in the range of 27° C. to 37° C., without growth at 50° C.
(2) Liquefaction of gelatin
(2-1) 15% gelatin—Weakly positive after 14 days of incubation at 20° C.
(2-2) Glucose-peptone-gelatin agar—Weakly or moderately positive after 7 days of incubation at 27° C.
(3) Hydrolysis of starch
Weak in starch-inorganic salts agar after 5 days of incubation at 27° C.
(4) Peptonization and coagulation of skim milk
Moderate to strong peptonization began after 5 days of incubation at 37° C., finishing in 17 days. No coagulation is seen.
(5) Formation of melanoid pigment
On incubation at 27° C., the production of melanoid pigment is observed in tryptone-yeast extract medium (ISP medium No. 1) and in peptone-yeast extract-ferrous ion agar (ISP medium No. 7).
(6) Utilization of carbon sources in Pridham-Gottlieb basal medium (ISP medium No. 9; incubated at 27° C.)
Abundant growth—L-Arabinose, D-xylose, D-glucose, D-fructose, sucrose, inositol, L-rhamnose and raffinose
No growth—D-Mannitol
(7) Liquefaction of calcium malate
Strong at 27° C. in calcium malate agar.
(8) Reduction of nitrate
Positive at 27° C. in peptone medium containing 1% sodium nitrate (ISP medium No. 8).

*Streptomyces galilaeus* KE 303 has been placed on permanent deposit with the culture collections of the American Type Culture Collection, Rockville, Md., and the Fermentation Research Institute, Japan its accession number being ATCC 31649 and FERM-P 4808, respectively.

For production of trisarubicinol according to the present invention, the above-defined converting microorganisms such as *Streptomyces galilaeus* KE 303 are first propagated to sporulation on agar slant medium containing 0.3% yeast extract, 1.0% soluble starch and 1.5% agar, pH 7.2. Then spores are inoculated into liquid medium containing nutrients such as starch, glucose, organic nitrogen sources and mineral salts and are cultivated under shaking at a temperature of 25°–32° C. for a period of 1–3 days to provide the seed culture.

The seed culture is then transferred at an inoculum size of 1–3% into a usually employed liquid fermentation medium composed of assimilable nutrients such as sucrose, glucose, soybean meal and mineral salts and is shake-cultured at a temperature of 25°–32° C. for a period of 15–48 hours to reach the logarithmic phase of growth. After 10–200 μg/ml (final concentration) of carminomycinone or dihydrocarminomycinone in methanol is added at this stage of cell growth, the culture broth is incubated for a further 15–72 hours until a substantial portion of the carminomycinone or dihydrocarminomycinone added is converted to trisarubicinol by microbial action. For control of foaming during incubation, a suitable amount of an anti-foaming agent such as Adecanol ® (Asahi Denka Co.) and Silicon ® (Shinetsu Chemical Co.) may be supplemented to the culture broth. The culture broth is filtered to give mycelia and filtrate. Crude pigments including trisarubicinol are extracted both from the mycelia and from the filtrate. Suitable extraction agents are acetone, methanol, chloroform, ethyl acetate, toluene, dilute mineral acids and acidic buffer solutions. Trisarubicinol is isolated and purified from crude pigments by an appropriate combination of conventional purification procedures such as column and thin layer chromatographies using silica gel (Wako Pure Chemical Industries and E.

Merck, Darmstadt), cross-linked dextran gel (Sephadex LH-20; Pharmacia Fine Chemical AB) and weakly acidic ion exchange resins; liquid chromatography and counter current distribution. For example, trisarubicinol is first separated from unchanged aglycone by gel filtration on cross-linked dextran gel such as Sephadex LH-20 and then repeatedly subjected to preparative silica gel thin layer chromatography (silica gel $PF_{254}$; E. Merck, Darmstadt) using varied solvent systems to provide a satisfactorily pure preparation of trisarubicinol.

Trisarubicinol may be produced in form of acid addition salts with inorganic or organic acids by conventional salification methods, as it has a dimethylamino group at the 3'-position (see above).

The evidence that the final product of the present invention is trisarubicinol represented by the abovedescribed structure (I) was presented by ultraviolet (UV) and visible spectrometry, infrared (IR) spectrometry, 100 $MH_z$ proton n.m.r. spectrometry (PMR), $^{13}C$-n.m.r. spectrometry (CMR), mass spectrometry and elementary analysis; and was additionally confirmed by qualitative analysis of the aglycone moiety and the sugar moieties in the acid hydrolysate by means of instrumental and thin layer chromatographic characterization.

The aglycone obtained from the product of the present invention by hydrolysis was identified to be dihydrocarminomycinone by comparing the observed analytical data with the physico-chemical properties reported in Antibiotiki 21, 1008 (1976). By employing the analytical methods which were described for structure determination of the sugar moieties of aclacinomycin A (J. Antibiotics 32, 801–819 (1979)), the composition, linking order and position of linkage with the aglycone of the constituent sugars were examined to show that trisarubicinol has the same glycoside structure as aclacinomycin A.

More particularly, L-rhodosamine is linked with the C-7 hydroxyl of dihydrocarminomycinone (aglycone substrate) (when carminomycinone is used as substrate, it is first converted to dihydrocarminomycinone before glycoside formation). Subsequently 2-deoxy-L-fucose and finally L-cinerulose A are attached through glycoside linkage to form trisarubicinol.

The physicochemical properties of trisarubicinol produced by the present invention are as shown below.
1. Appearance—Dark red powder
2. Melting point—149°–152° C.
3. Molecular weight—785.84
4. Elementary analysis for $C_{40}H_{51}NO_{15}$

|  | C | H | N | O |
|---|---|---|---|---|
| Calculated (%) | 61.14 | 6.54 | 1.78 | 30.54 |
| Found (%) | 60.62 | 6.47 | 1.93 | — |

5. Optical rotation—$[\alpha]_D^{23}$ +1.84° (c 0.8, $CHCl_3$).
6. Ultraviolet and visible absorption spectrum

| | | |
|---|---|---|
| $\lambda_{max}^{90\% \ MeOH}$ nm($E_{1 \ cm}^{1\%}$) | 234(419) | 254(342) |
| | 292(95) | 465(125) |
| | 493(162) | 514(120) |
| | 526(117) | 575(15) |
| $\lambda_{max}^{90\% \ MeOH-0.1N \ HCl}$ nm($E_{1 \ cm}^{1\%}$) | 234(434) | 254(352) |
| | 292(100) | 465(135) |
| | 493(172) | 514(122) |
| | 526(115) | |
| $\lambda_{max}^{90\% \ MeOH-0.1N \ NaOH}$ nm($E_{1 \ cm}^{1\%}$) | 241(482) | 286(92) |
| | 560(181) | 596(154) |

7. Infrared spectrum (KBr): $\nu cm^{-1}$: 1720, 1600, 1290, 1005.
8. Proton n.m.r. spectrum (100 MHz; $CDCl_3$): δppm: 1.18(d, 6'-$CH_3$), 1.28(d, 6''-$CH_3$), 1.34(d, 6'''-$CH_3$), 1.9-(m, 2'-$CH_2$, 2''-$CH_2$), 2-(m, 2'''-$CH_2$), 2.19(s, N($CH_3$)$_2$), 2.4-(m, 8-$CH_2$, 3'-H, 3'''-$CH_2$), 2.88(dd, 10-$CH_2$), 3.67(broad, 4''-H), 3.76(broad, 4'-H), 4.02(q, 5''-H), 4.1-(m, 3''-H), 4.50(q, 5'''-H), 4.56(q, 5'-H), 4.6(broad, 9-OH), 5.03(broad, 1''-H), 5.07(t, 1'''-H), 5.24(broad, 7-H), 5.52(broad, 1'-H), 7.26(dd, 3-H), 7.68(t, 2-H), 7.81(dd, 1-H), 12.1 & 13.4(4, 6, 11-OH).

The utility of the product of the present invention is explained in the following:

The compound of the present invention markedly inhibits the growth and nucleic acid synthesis in cultured cells of mouse leukemia (L1210). The 50% inhibitory concentration of trisarubicinol on L1210 leukemia cells was calculated by culturing $5 \times 10^4$ cells/ml at 37° C. in 5% $CO_2$-air in 20% calf serum-supplemented RPMI 1640 medium (Roswell Park Memorial Institute 1640 medium) containing none (control), 0.01 and 0.05 μg/ml of trisarubicinol. In addition. the inhibitory effect of the new anthracycline compound on nucleic acid synthesis was examined as follows: after $5 \times 10^5$ cells/ml of L1210 leukemia cells were preincubated in 5% $CO_2$-air at 37° C. for 1–2 hours in RPMI medium containing 10% calf serum, varied concentrations of trisarubicinol were added and incubated for 15 minutes under the same conditions. Then 0.05 μCi/ml each of $^{14}C$-uridine or $^{14}C$-thymidine was added to the cell suspensions and the mixtures were incubated at 37° C. for a further 60 minutes. At the end of incubation, cold 10% trichloroacetic acid was added to stop the incorporation of the radio-labelled compound. The acid-insoluble fractions were collected by centrifugation; rinsed three times with 5% trichloroacetic acid; and dissolved in formic acid for radiometry. The 50% inhibitory concentration of the new anthracycline compound was calculated from the radiometric data of the acid-insoluble fractions of the control and test reaction mixtures.

The therapeutic effect of trisarubicinol was examined by calculating the prolongation of the survival time of treated animals relative to untreated ones (receiving physiological saline). In practice, $1 \times 10^5$ mouse leukemia cells each were intraperitoneally transplanted into $CDF_1$ mice and varied doses of trisarubicinol were intraperitoneally injected every day for 10 days from 24 hours after cell transplantation.

Table 1 summarizes the antitumor effect on L1210 leukemia cells and the toxicity data of trisarubicinol.

TABLE 1

Antitumor effect and toxicity of trisarubicinol (1) In vitro activity on L1210 leukemia culture cells

| | 50% inhibitory concentration ($IC_{50}$ in μg/ml) | |
|---|---|---|
| | trisarubicinol | carminomycin I |
| Cell growth inhibition | 0.01 | 0.01 |
| DNA synthesis inhibition | 0.38 | 0.20 |
| RNA synthesis inhibition | 0.06 | 0.29 |

(2) In vivo activity on L1210 mouse leukemia

TABLE 1-continued

Antitumor effect and toxicity of trisarubicinol

|  | dose of trisarubicinol (%) | prolongation of survival time (T/C in %) |
|---|---|---|
|  | 10 | 131 |
|  | 7.5 | 243 |
|  | 5.0 | 216 |
|  | 2.5 | 159 |
|  | 1.25 | 124 |
|  | 0.63 | 122 |
| (3) Acute toxicity | LD$_{50}$ in mg/kg, i.p. | 40–50 |

The above-described results clearly indicate that trisarubicinol prepared by the present invention significantly inhibits the growth of L1210 mouse leukemia cells at low doses and have a marked prolonging effect on the survival time of leukemia cells-holding mice. Although the target site of action of anthracycline compounds is reported to be the nucleic acid synthesis, the compound of the present invention differs from carminomycin I in the better inhibition of RNA synthesis at very low concentrations, suggesting that the mode of inhibition of trisarubicinol is similar to those of aclacinomycins and rhodomycins. Furthermore, in spite of the same or better antitumor activity, trisarubicinol is less toxic than carminomycin I.

The examples which follow illustrate the present invention in detail.

EXAMPLE 1

One loopful of spores were collected from the agar slant culture of *Streptomyces galilaeus* KE 303; and inoculated into a 500 ml Erlenmeyer flask containing 100 ml of sterile seed medium composed of 1.5% soluble starch, 1.0% glucose, 1% soybean meal, 0.1% yeast extract, 0.3% sodium chloride, 0.1% dipotassium phosphate, 0.1% MgSO$_4$.7H$_2$O, 0.0007% CuSO$_4$.5H$_2$O, 0.0001% FeSO$_4$.7H$_2$O, 0.0008% MnCl$_2$.4H$_2$O and 0.0002% ZnSO$_4$.7H$_2$O, pH 7.4. Shaking culture at 28° C. for 48 hours on a rotary shaker gave the seed culture. One milliliter each of the seed culture was transferred into thousand of 500-ml Erlenmeyer flasks containing 50 ml each of fermentation medium, the composition of which was the same as the above-described seed medium except that the amounts of soybean meal and yeast extract were increased by 3.0% and 0.2% respectively. The flasks were incubated under shaking at 28° C. for 17 hours on a rotary shaker (210 rpm). A half milliliter each of 1 mg/ml carminomycinone (final concentration 10 μg/ml; 500 mg in total) was poured into the flasks and incubated for a further 24 hours under the same conditions.

For determination of the conversion percentage of carminomycinone to trisarubicinol at the end of fermentation, 5 ml of the broth was mixed thoroughly with 5 ml of a chloroform-methanol mixture on a Thermomixer ®. The chloroform extract was separated, concentrated to dryness and dissolved in 0.2 ml of chloroform. Twenty microliters of the chloroform solution was spotted on a silica gel thin layer plate (pre-coated thin layer plate silica gel 60 F$_{254}$; E. Merck, Darmstadt) and developed in a solvent system of chloroform/methanol/ammonia water (100/100/0.3). After the solvent was evaporated off, spots of trisarubicinol (Rf 0.79), unchanged carminomycinone (Rf 0.67) and dihydrocarminomycinone (reduction product of carminomycinone; Rf 0.43) were quantitated in a Shimadzu thin layer chromato-scanner CS-910. Based on the analytical data, about 30% of the aglycone added was calculated to be used in the conversion reaction, meaning that 142 mg in total of trisarubicinol was produced.

The broth was collected from the flasks (50 liters in total) and centrifuged. The mycelia was recovered and suspended in 8 liters of acetone for extraction. After the acetone extract was concentrated to about one third of the original volume, the product was transferred into 3 liters of chloroform. Evaporation of the chloroform yielded a crude preparation of trisarubicinol.

EXAMPLE 2

The crude preparation of trisarubicinol obtained in Example 1 was dissolved in 100 ml of chloroform/methanol (1/2, v/v). After insoluble matters were removed by centrifugation, 50 ml each of the supernatant solution was charged on a Sephadex LH-20 column (5.0×40 cm) and developed with a chloroform-methanol mixture (1/2, v/v). The first coming red pigment fractions were pooled and concentrated to dryness. The evaporation residue was dissolved in a small volume of chloroform and applied in linear fashion 1.5 cm from the bottom edge on 25 silica gel thin layer plates (Kieselgel 60 PF$_{254}$; E. Merck, Darmstadt) and developed in a solvent system of chloroform and methanol (20/1, v/v).

The areas of silica gel of trisarubicinol at Rf 0.2 were scraped off and trisarubicinol was eluted from the silica gel with 200 ml of a solvent mixture of chloroform/methanol/ammonia water (100/15/0.2, v/v/v). The eluate was concentrated to dryness under reduced pressure. The residue was dissolved in 0.1 M acetate buffer, pH 3.5; rinsed with toluene for removal of oily impurities; and adjusted to pH 7.0 with sodium bicarbonate. Trisarubicinol was extracted from the aqueous solution with chloroform. As a small amount of red impurities were present, the chloroform extract was concentrated to a small volume in vacuo and subjected to preparative thin layer chromatography. A solvent mixture of chloroform/methanol/ammonia water (100/10/0.1, v/v/v) was used for column development, whereas the same mixture with a different mixing ratio (100/15/0.2, v/v/v) was for elution from silica gel. The eluate was concentrated to dryness under reduced pressure and dissolved again in 0.1 M acetate buffer, pH 3.5. After rinsing with toluene, the aqueous solution was adjusted to pH 7.0 with sodium bicarbonate. Trisarubicinol was extracted from the aqueous solution with chloroform. The chloroform extract was dried over anhydrous sodium sulfate and concentrated to 2.5 ml in vacuo. Forced precipitation with n-hexane followed by desiccation provided 42 mg of dark red powder of trisarubicinol which showed the above-described physico-chemical properties.

EXAMPLE 3

According to the same procedure as detailed in Example 1, *Streptomyces galilaeus* KE 303 was cultivated for microbial conversion of 500 mg of dihydrocarminomycinone. The conversion percentage was found to be about 35% for the crude extract. The crude extract was purified by the same procedure as explained in Example 2, resulting in 58 mg of pure trisarubicinol.

What is claimed is:

1. A compound represented by the chemical structure

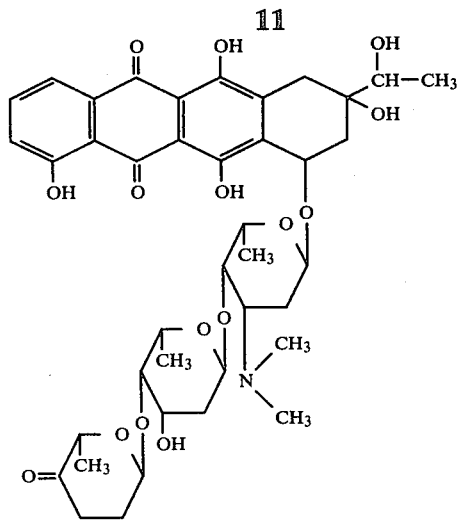
or its acid addition salts.
* * * * *